United States Patent
Hefner, Jr. et al.

(10) Patent No.: US 6,365,788 B1
(45) Date of Patent: Apr. 2, 2002

(54) PREPARATION OF 1,2-BIS(4-HYDROXYPHENYL)-2-HYDROXYPROPANES

(75) Inventors: Robert E. Hefner, Jr.; Katherine S. Clement, both of Lake Jackson; Lance L. Black, Richwood; Louis L. Walker, Clute, all of TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/625,934

(22) Filed: Jul. 26, 2000

Related U.S. Application Data
(60) Provisional application No. 60/146,276, filed on Jul. 29, 1999.

(51) Int. Cl.$^7$ .............................................. C07C 39/12
(52) U.S. Cl. ...................................................... 568/729
(58) Field of Search ......................................... 568/729

(56) References Cited

U.S. PATENT DOCUMENTS

| | | | |
|---|---|---|---|
| 2,349,770 A | * | 5/1944 | Tendick |
| 2,385,853 A | * | 10/1945 | Turnbull |
| 3,066,112 A | | 11/1962 | Bowen |
| 3,179,623 A | | 4/1965 | Bowen |
| 3,256,226 A | | 6/1966 | Fekete et al. |
| 3,301,743 A | | 1/1967 | Fekete et al. |
| 3,367,992 A | | 2/1968 | Bearden |
| 3,892,819 A | | 7/1975 | Najvar |
| 4,156,787 A | * | 5/1979 | Coleman |
| 4,189,610 A | * | 2/1980 | Coleman |
| 5,164,464 A | | 11/1992 | Hefner et al. |
| 5,414,150 A | | 5/1995 | Hefner, Jr. et al. |
| 5,475,155 A | | 12/1995 | Hefner, Jr. et al. |
| 5,686,551 A | | 11/1997 | White et al. |
| 5,723,692 A | | 3/1998 | Clement et al. |
| 5,723,693 A | | 3/1998 | Hefner, Jr. et al. |
| 5,736,620 A | | 4/1998 | Earls et al. |

OTHER PUBLICATIONS

Spivack, Leib and Lobos, Novel Pathway for Bacterial Metabolism of Bisphenol A, "The Journal of Biological Chemistry", vol. 269, No. 10, pp. 7323–7329, 1994.

L. R. Whittington, *Whittington's Dictionary of Plastics*, p. 239, 1968.

"Studies in the Photodimerization of the Diglycidyl Ether of 4, 4'–Dihydroxychalcone", Journal of Polymer Science, vol. 23, pp. 1355–1372, John Wiley & Sons, Inc. 1979., Zahir.

G. G. Odian, Principles of Polymerization, John Wiley & Sons, pp. 179–507, 1981.

* cited by examiner

*Primary Examiner*—Michael L. Shippen

(57) ABSTRACT

The present invention relates to the preparation of substituted or unsubstituted 1,2-bis(4-hydroxyphenyl)-hydroxyaliphatics such as 1,2-bis(4-hydroxyphenyl)-2-hydroxypropanes by reacting substituted or unsubstituted 1,2-bis(4-hydroxyphenyl)-halogen substituted aliphatics such as 1,2-bis(4-hydroxyphenyl)-2-chloropropanes in the presence of a base and water.

23 Claims, No Drawings

PREPARATION OF 1,2-BIS(4-HYDROXYPHENYL)-2-HYDROXYPROPANES

This application claims the benefit of U.S. Provisional Application No. 60/146,276, filed Jul. 29, 1999.

FIELD OF THE INVENTION

The present invention concerns a process for the production of a substituted or unsubstituted 1,2-bis(4-hydroxyphenyl)-hydroxyaliphatic from a substituted or unsubstituted 1,2-bis(4-hydroxyphenyl)-haloaliphatic. More particularly, the present invention concerns a process for the production of 1,2-bis(4-hydroxyphenyl)-2-hydroxypropane from 1,2-bis(4-hydroxyphenyl)-2-chloropropane.

BACKGROUND AND SUMMARY OF THE INVENTION

Compounds such as 4,4'-dihydroxy-α-methylstilbenes are often useful as intermediates in the production of liquid crystal thermosets and thermoplastics. The aforementioned stilbenes are often prepared from compounds such as 1,2-bis(4-hydroxyphenyl)-2-chloropropanes. Unfortunately, however, compounds such as 1,2-bis(4-hydroxyphenyl)-2-chloropropanes must be stored in dilute concentrations at low temperatures (<15° C.) or decomposition will occur. Moreover, the process for converting the 1,2-bis(4-hydroxyphenyl)-2-chloropropane to the corresponding stilbene is disadvantageous in that hydrogen chloride, a difficult to handle co-product, is produced.

Alternate processes would be desirable in order to overcome the aforementioned problems associated with using the starting material 1,2-bis(4-hydroxyphenyl)-2-chloropropane when making stilbenes, i.e., the problems of storage and producing hydrogen chloride co-product. One alternate process would involve the dehydration of a substituted or unsubstituted 1,2-bis(4-hydroxyphenyl)-hydroxyaliphatic such as 1,2-bis(4-hydroxyphenyl)-2-hydroxypropane. In contrast to 1,2-bis(4-hydroxyphenyl)-2-chloropropane, compounds such as 1,2-bis(4-hydroxyphenyl)-2-hydroxypropane are often storable at ambient conditions and would only produce water as a co-product when preparing 4,4'-dihydroxy-α-methylstilbenes. Unfortunately, however, there are no prior synthetic methods of preparing discreet compounds such as 1,2-bis(4-hydroxyphenyl)-2-hydroxypropane.

A prior method of preparing 1,2-bis(4-hydroxyphenyl)-2-hydroxypropane is described in Spivack, Leib and Lobos in *The Journal of Biological Chemistry*, Volume 269, No. 10, pages 7323–7329 (1994). The complex chemical and biological route described by Spivack et al. first involved the production of 1,2-bis(4-methoxyphenyl)-2-propanol in an unspecified yield via reaction of 4-methoxyphenyl magnesium bromide and 4-methoxyphenylacetone in dry tetrahydrofuran. Spivack et al. could not demethylate the 1,2-bis(4-methoxyphenyl)-2-propanol without substantial dehydration of the product to 4,4'-dihydroxy-α-methylstilbene. Therefore, in order to obtain 1,2-bis(4-hydroxyphenyl)-2-hydroxypropane Spivack et al. conducted a biochemical demethylation in the presence of the fungus, *Aspergillus parasiticus*. Isolation methods to recover the product from the biologic medium are not given, but are expected to be complex and to produce low yields of an impure product, based on their reported isolation of 1,2-bis(4-hydroxyphenyl)-2-hydroxypropane as a bisphenol A metabolite in a biologic medium.

Therefore, it would be desirable to discover a synthetic process to prepare 1,2-bis(4-hydroxyphenyl)-hydroxyaliphatics such as 1,2-bis(4-hydroxyphenyl)-2-hydroxypropane in a simple manner with a good yield.

Advantageously, the present invention pertains to a process to prepare 1,2-bis(4-hydroxyphenyl)-hydroxyaliphatics such as 1,2-bis(4-hydroxyphenyl)-2-hydroxypropane in a simple manner with a good yield. The inventive process relates to producing a compound having the structural Formula I

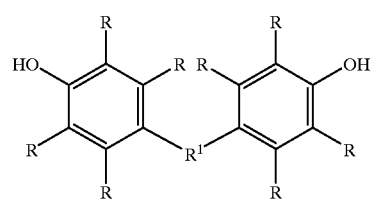

wherein R is independently selected from the group consisting of hydrogen, a hydrocarbyl group having from 1 to about 12 carbon atoms, a hydrocarbyloxy group having from 1 to about 12 carbon atoms, a halogen atom, and a nitro group, and $R^1$ is a hydroxyl substituted aliphatic group having from 3 to about 8 carbon atoms. The process comprises reacting a compound having the structural Formula II,

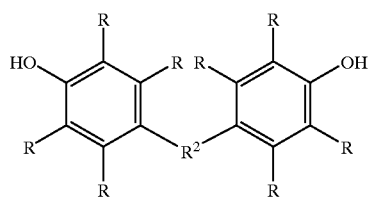

wherein R is as described above and $R^2$ is a halogen substituted aliphatic group having from 3 to about 8 carbon atoms with a base and water, and wherein (1) the base is selected from the group consisting of an alkali metal carbonate, alkaline earth metal carbonate, an alkali metal bicarbonate, an alkaline earth metal bicarbonate, and mixtures thereof;

(2) the equivalent ratio of base to halogen in the aliphatic group is from about 0.9:1 to about 5:1; and (3) the amount of water is from about 20 to about 500 percent by weight of the combined weight of the compound of Formula II and water.

The present invention also relates to novel, synthetic, compounds having structural Formula V

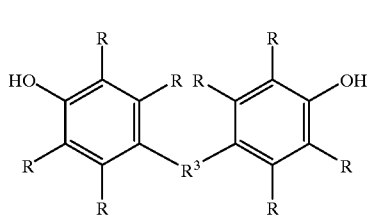

wherein R is independently selected from the group consisting of hydrogen, a hydrocarbyl group having from 1 to about 12 carbon atoms, a hydrocarbyloxy group having from 1 to about 12 carbon atoms, a halogen atom, and a nitro group; $R^3$ is an alkylene group having from 3 to about 8 carbon atoms substituted with one or more hydroxyl groups. In a particular aspect, if all R groups are hydrogen then $R^3$ is not —C(CH$_3$)(CH$_2$OH)—, —CH$_2$C(OH)(CH$_2$OH)—, —C(CH$_2$OH)(CH$_2$OH)—.

DETAILED DESCRIPTION OF THE INVENTION

As used herein, the term "hydrocarbyl" means any substituted or unsubstituted aliphatic, cycloaliphatic, aromatic, aryl substituted aliphatic, aryl substituted cycloaliphatic, aliphatic substituted aromatic, or cycloaliphatic substituted aromatic group. The aliphatic or cycloaliphatic group groups can be saturated or unsaturated. The aliphatic groups can be straight chain or branched. Suitable substituents include any substituent which does not substantially interfere with the reaction.

As used herein, the term "hydrocarbyloxy" means a hydrocarbyl group having an oxygen linkage between it and the atom to which it is attached.

As used herein, the term "hydroxyl substituted aliphatic" or "hydroxyaliphatic" means an aliphatic group, such as alkylene or alkenylene, which is substituted with one or more hydroxyl groups and is divalent, i.e., has two attachment points as shown for $R^1$ in Formula I. Similarly, the term "halogen substituted aliphatic" or "haloaliphatic" means an aliphatic group, such as alkylene or alkenylene, which is substituted with one or more halogen groups and is divalent, i.e., has two attachment points as shown for $R^2$ in Formula II.

As used herein, the term "polar protic solvent" means a compound which serves as a solvent and has a high dielectric constant and strong polarity. For the purpose of the present invention, "polar protic solvent" means that the compound contains at least one hydroxyl group.

As used herein, the term "synthetic" means that the compound is prepared via a non-biological route, i.e., the compound is not prepared, for example, via bacterial metabolism.

Generally, the inventive process relates to producing a compound having the structural Formula I

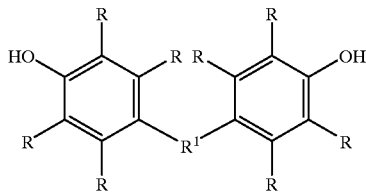

wherein R is independently selected from the group consisting of hydrogen, a hydrocarbyl group having from 1 to about 12 carbon atoms, a hydrocarbyloxy group having from 1 to about 12 carbon atoms, a halogen atom, and a nitro group, and $R^1$ is an hydroxyl substituted aliphatic group having from 3 to about 8 carbon atoms. Preferably R is hydrogen and $R^1$ is a hydroxyl substituted alkylene group. Preferable alkylene groups include propylene, and butylene. Preferable substituted alkylene groups include —C(CH$_3$)(OH)CH$_2$— and —C(CH$_2$OH)(CH$_2$OH)—.

The process comprises reacting a compound having the structural Formula II with a base and water,

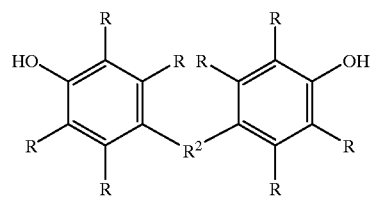

wherein R is as described above and $R^2$ is a halogen substituted aliphatic group having from 3 to about 8 carbon atoms. Preferably R is hydrogen and $R^2$ is a halogen substituted alkylene group. Preferable alkylene groups include propylene and butylene. Preferable halogens include chlorine and bromine. Preferable substituted alkylene groups include —C(CH$_3$)(X)CH$_2$— and —C(CH$_2$X)(CH$_2$X)—, wherein X represents —Cl, —Br, or —I.

A particularly preferred embodiment is a process for producing a compound having the structural Formula III

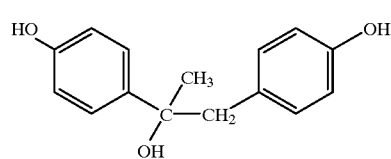

by reacting a compound having the structural Formula IV

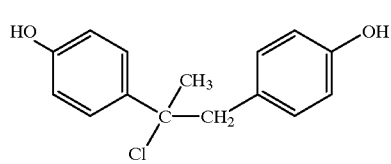

with a base, water, and in the presence of a polar protic solvent.

The present invention also relates to novel, synthetic compounds having structural Formula V

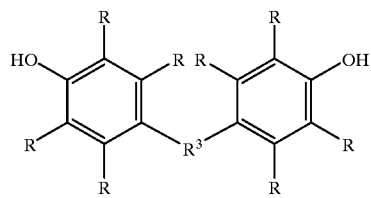

wherein R is independently selected from the group consisting of hydrogen, a hydrocarbyl group having from 1 to about 12 carbon atoms, a hydrocarbyloxy group having from 1 to about 12 carbon atoms, a halogen atom and a nitro group; $R^3$ is an alkylene group having from 3 to about 8 carbon atoms substituted with one or more hydroxyl groups. In a particular aspect, if all R groups are hydrogen then $R^3$ is not —C(CH3)(CH20H)—, —CH$_2$C(OH)(CH$_2$OH)—, or —C(CH$_2$OH)(CH$_2$OH)—.

Reaction Mixture

The starting ingredients of the present invention typically comprise a compound of Formula II, a base, and water. The compound of Formula II may be and preferably is in the form of a mixture as explained in detail below. Preferably, a polar protic solvent may also be employed.
Compound of Formula II The starting compounds which are useful in the process of the present invention have the structural Formula II

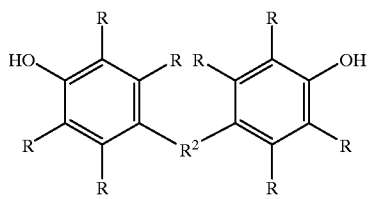

wherein R is as described above and $R^2$ is a halogen substituted aliphatic group having from 3 to about 8 carbon atoms. Preferably R is hydrogen and $R^2$ is a halogen substituted alkylene group. Preferable alkylene groups include propylene and butylene. Preferable halogens include chlorine and bromine. Preferable substituted alkylene groups include —C(CH$_3$)(X)CH$_2$— and —C(CH$_2$X)(CH$_2$X)— wherein X represents Cl, Br, or I.

Said compounds of structural Formula II may be employed alone or as part of a mixture. The method of preparing the compounds of Formula II is not critical. Suitable methods are described in, for example, U.S. Pat. Nos. 5,414,150; 5,475,155; 5,723,693; and 5,723,692; all of which are incorporated herein by reference in their entirety. When compounds of Formula II are prepared according to the aforementioned patents, the compounds are often obtained as a dilute, cold (15° C. or less) mixture comprising, for example, compounds of Formula II, a phenol, an acid, minor amounts of various co-products produced in the reaction, optionally an α-haloketone, and optionally a water-immiscible solvent such as, for example, methylene chloride.

A preferred mixture comprising a compound of Formula II is 1,2-bis(4-hydroxyphenyl)-2-chloropropane prepared using the methods of the aforementioned U.S. Pat. No. 5,723,692 and phenol, chloroacetone, sulfuric acid or methanesulfonic acid, and methylene chloride as reactants and a water-immiscible solvent, respectively.

If an acid is present as part of the reactant mixture, then it is often preferable to substantially remove the acid in order to facilitate the production of the desired product during the reaction. The acid may be removed by any means but often a washing of the mixture with cold water is sufficient. As described below, the acid may also be neutralized by the addition of the base to be employed in the reaction.
Base Suitable bases or basic acting substances which can be employed as a reactant herein include any such substance or mixture of substances which hydrolyze, i.e., convert, the halogen substituted aliphatic group to a hydroxyl substituted aliphatic group. Suitable bases include, for example, the alkali metal and alkaline earth metal carbonates and or alkali metal and alkaline earth metal bicarbonates. Suitable such carbonates and bicarbonates include, for example, lithium carbonate, sodium carbonate, potassium carbonate, calcium carbonate, strontium carbonate, cesium carbonate, rubidium carbonate, barium carbonate including α-, β-, and γ-barium carbonate, magnesium carbonate including Mg(CO$_3$).Mg(OH$_2$).3H$_2$O, 3Mg(CO$_3$).Mg(OH$_2$).3H$_2$O, lithium bicarbonate, sodium bicarbonate, potassium bicarbonate, cesium hydrogen carbonate, rubidium acid carbonate, as well as, hydrates and mixtures thereof. Preferred bases are the alkaline earth metal carbonates. Most preferred bases are magnesium carbonate, calcium carbonate, strontium carbonate, or mixtures thereof. Bases which are least preferable are those such as alkali metal hydroxides because extensive undesirable side products are produced.

The equivalent ratio of base or basic acting substance to halogen group which substitutes the aliphatic group is a sufficient ratio to obtain the desired product in the desired yield. Typically, the equivalent ratio of base to halogen is from about 0.9:1 to about 5:1, preferably from about 1:1 to about 2:1, most preferably from about 1.1:1 to about 1.5:1. The aforementioned ranges do not consider residual acid which may be present in an initial mixture comprising a compound of Formula II. If the acid is not removed or neutralized then adjustment of the aforementioned amounts of base may be desirable in order to neutralize any residual acid present in the mixture comprising a compound of Formula II. In this manner, the reaction to form the desired product is facilitated and the production of by-products is minimized.

Typically, when the equivalent ratios described above are employed, the pH of the reaction will generally be above about 5,. preferably above about 7. A pH of above about 5, preferably above about 7 is desirable in order to avoid the conversion of the compounds of Formula I to the corresponding stilbene via a dehydrochlorination or dehydration reaction. For example, if the pH falls below about 5 during the production of 1,2-bis(4-hydroxyphenyl)-2-hydroxypropane from 1,2-bis(4-hydroxyphenyl)-2-chloropropane then 4,4'-dihydroxy-α-methylstilbene may result. For the aforementioned reasons, if a large amount of acid is present in the initial mixture comprising Formula II, then it is preferable to substantially remove or substantially neutralize the acid such that the pH is above about 5, preferably above about 7, during the reaction to form the compounds of Formula I. One manner of neutralizing the acid is to use an amount of the base described above such that the pH of the reaction mixture is above about 5, preferably above about 7.
Water The amount of water employed may vary depending upon the amount of water in the initial ingredients, if any, the amount of water need to suspend, partially dissolve or fully dissolve the base, and other such variables. However, typically water is employed in an amount of from about 20 to about 500, preferably from about 40 to about 300, most preferably from about 60 to about 150 percent by weight of the combined weight of the compound of Formula II and water. The aforementioned quantities of water are the quantities necessary in order for the water to serve as a reactant and a reaction medium. If, for example, a less water-soluble base is employed then additional water may be necessary. Stirring or mixing is often desirable while adding water, and during the reaction. In this manner, complete dispersion of the water and even heating of the reactants is facilitated.
Polar Protic Solvent The polar protic solvent is not critical for the process of the present invention but is often preferred depending on the starting ingredients and other parameters which are to be employed. The polar protic solvents useful herein include, for example, aliphatic alcohols, glycols, glycol ethers, and mixtures thereof. Such solvents include, for example, methanol, ethanol, n-propanol, isopropanol, n-butanol, isobutanol, t-butanol, t-amyl alcohol, ethylene glycol, ethylene glycol monomethylether, ethylene glycol monoethylether, propylene glycol monomethylether, as well as, mixtures thereof. More preferred polar protic solvents include ethanol, n-propanol and isopropanol, with ethanol and isopropanol being most preferred.

The amount of polar protic solvent used, if any, varies depending upon the amount of water used, the need to suspend, partially dissolve or fully dissolve the basic acting substance, the dispersion of reactants, and other such variables. Typically, the polar protic solvent is used in an amount of less than about 500, preferably from about 50 to about 300, most preferably from about 75 to about 150 percent by weight of the combined weight of the compound of Formula II and polar protic solvent used. The polar protic solvent, if used, often serves as a medium for the hydrolysis reaction, solvates the product preventing its premature precipitation, and/or modifies the dispersion of the various reactants, for example, inducing formation of a single phase reaction mixture versus a two-phase reaction mixture.

Process

The process of the present invention may be conducted as a continuous or batch process. Similarly, many different atmospheres may be employed, however, it is often preferable to conduct the reaction in an inert atmosphere such as nitrogen.

In the process of the present invention, the compound of Formula I, alone or in a mixture, is reacted with a base and water. As described above, a polar protic solvent may also be employed.

While the ingredients may be mixed together in any order, it is often preferable to first mix the base, water and, optionally, the polar protic solvent at ambient conditions. The mixture comprising base, water, and, optionally, solvent may then be heated to the desired reaction temperature which is described below. The compound of Formula II or mixture comprising a compound of Formula II is then added either incrementally or in bulk to the mixture comprising base, water, and, optionally, solvent, while a desirable reaction temperature is reached and maintained until the substantial completion of the reaction. During the reaction, mixing or stirring is often desirable to assure an even temperature of the reaction mixture and complete dispersion of the reactants.

Suitable temperatures, pressures, and times of the reaction often vary depending upon the starting ingredients. The reaction may be conducted at atmospheric, reduced, or increased pressure, but it is often advantageous to employ a temperature and pressure at which the starting ingredients are in a liquid form, i.e., the temperature and pressure are not such that one or more ingredients freezes or boils. In this manner, the ingredients are easily measured and metered into the reaction vessel.

Preferably, the reaction is conducted at atmospheric pressure at a temperature of from about 0° C. to about 100° C., preferably from about 25° C. to about 80° C., more preferably from about 40° C. to about 70° C.

The reaction time will vary depending upon the starting ingredients, pressure, temperature, solubility of the base and other such variables. Typically, the reaction mixture is maintained at the reaction temperature for a sufficient time to hydrolyze, i.e., convert, the halogen substituted aliphatic group to a hydroxyl substituted aliphatic group. Generally, the higher the reaction temperature is, the shorter the period of time that the reaction requires. Correspondingly, the lower the reaction temperature is, the longer the period of time that the reaction requires.

At atmospheric pressure and temperatures of from about 0° C. to about 100° C., the reaction time is typically from about 30 minutes to about 48 hours, preferably from about 60 minutes to about 24 hours, more preferably from about 2 hours to about 12 hours.

In the process of the present invention, it is typically desirable to choose a reaction time and temperature profile and a manner of contacting the ingredients together which provides the greatest conversion and selectivity of the desired compound of Formula I. Thus, it is frequently of value to conduct simple preliminary experiments over the range of variables which can be employed in order to define an optimum reaction time, temperature, and manner of contacting the ingredients which provides the greatest conversion and selectivity to the desired compound of Formula I. In this manner, conditions are obtained which are conducive to optimizing the yield of the desired compound of Formula I which is substantially free of unwanted coproducts.

In the preliminary experiments and the process of the present invention, it is frequently desirable to monitor the course of the reaction via an analytical method, such as high pressure liquid chromatographic analysis (HPLC).

During the course of the reaction, water-immiscible solvents such as methylene chloride may be introduced into the reaction product via an original mixture comprising a compound of Formula II. It is preferable to allow such water-immiscible solvent or solvents, if present in large amounts, to evaporate or distill from the stirred, heated mixture during the course of the reaction and after the reaction. This distillation may be assisted by the application of a gentle vacuum during the reaction, although care must be taken not to remove other ingredients from the reaction mixture, i.e., compounds of Formula II, bases, water, or optional polar protic solvents.

Recovery of the Product

The recovery of the compounds of Formula I from the reaction product should be performed using conditions and methods which preserve the majority of the product. Thus, evaporation, distillation, vacuum distillation, rotary evaporation, falling film distillation, wiped film distillation, or other such methods may be advantageously employed to remove volatile materials, such as, for example, phenol-water azeotrope, any residual water-immiscible solvent, and polar protic solvent.

When employing azeotropic distillation it is often preferred to use a reduced pressure. In the course of such azeotropic distillation, water may be added or removed from the reaction product, as needed, to facilitate recovery and isolation of the compound of Formula I. The presence of water often serves to assist azeotropic removal of phenols which may be introduced into the reaction product via an original mixture comprising a compound of Formula II. The azeotropic removal of phenol under aqueous conditions typically induces precipitation of the 1,2-bis(4-hydroxyphenyl)-2-hydroxypropane as a crystalline product. Thus, recovery of the product is facilitated.

The amount of water employed in the course of azeotropic distillation may vary depending upon the amount of the phenol present, the structure of the phenol present, the amount of water used in the reaction, and other such variables. Typically, water is employed during azeotropic distillation in an amount of from about 10 to about 500, preferably from about 25 to about 300, most preferably from about 50 to about 200 percent by weight of the combined weight of the reaction product and water.

For certain reaction products, wherein minor amounts of co-products are present, it is frequently advantageous to leave a minor amount of phenol in the aqueous crystalline slurry as a solvent for said coproducts. The crystalline compounds of Formula I may be recovered from aqueous slurry using any unit operations which effectively remove the crystals from said slurry, such as, for example, filtration or centrifugation followed by water washing to remove any salts. It is frequently useful to conduct simple preliminary experiments over the range of time and temperature at which the crystalline slurry can be held in order to define an optimum time and temperature profile which provides the greatest isolated yield of the desired compound of Formula I.

The compound of Formula I, once isolated, is advantageously maintained as a wet product stored at a reduced temperature to avoid decomposition. The recovered product may be utilized as a wet cake, or dried, for example under vacuum at temperatures which are not deleterious to said product, typically below 30° C. The compounds of Formula I may be converted to, for example, stilbenes by any suitable method. Suitable methods include those described in U.S. Pat. Nos. 5,414,150; 5,475,155; 5,723,693; and 5,723,692; all of which are incorporated herein by reference in their entirety.

Conversion to Stilbene

In the process of the present invention wherein a substituted or unsubstituted 1,2-bis(4-hydroxyphenyl)-hydroxyaliphatic is converted to the corresponding stilbene compound, any protic acid, Lewis acid, or mixture thereof may be employed to catalyze the dehydration reaction. Such acids are defined and examples listed in the patent references previously mentioned and incorporated herein by reference. Examples of additional such acids include sodium hydrogen sulfate, potassium hydrogen sulfate, acetic acid, phosphoric acid, phosphorous acid, sulfurous acid, trichloroacetic acid, and trifluoroacetic acid. Also, simple heating of the neat 1,2-bis(4-hydroxyphenyl)-hydroxyaliphatic to temperatures in excess of about 30° C. can induce conversion to the corresponding stilbene compound, due to the presence of trace acidic components, such as sulfonic acid(s), sulfuric acid, alkanesulfonic acid(s), hydrochloric acid, mixtures thereof and the like, all or some of which may be present in the 1,2-bis(4-hydroxyphenyl)-hydroxyaliphatic depending on it's synthetic history. Additionally, trace amounts of halogen-containing coproducts which may be present in the 1,2-bis(4-hydroxyphenyl)-hydroxyaliphatic, may serve as a source of hydrogen halide upon heating.

Because of the concomitant formation of substantial amounts of dimeric coproducts in the dehydration reaction of neat 1,2-bis(4-hydroxyphenyl)-hydroxyaliphatic, it is more preferred to conduct the reaction in one or more solvents, such as, for example, water, polar protic solvents, or mixtures thereof and the like. Said solvents are useful to dissolve the acid catalyst and assist its transfer in the reaction medium, to dissolve or suspend the 1,2-bis(4-hydroxyphenyl)-hydroxyaliphatic, and to provide dilution needed to minimize formation of dimeric coproducts. Most preferred are the solvents and reaction conditions given for the dehydrohalogenation reaction of 1,2-bis(4-hydroxyphenyl)-haloaliphatics in the patent references previously mentioned and incorporated herein by reference, especially those found in U.S. Pat. No. 5,723,692.

EXAMPLE 1

In situ Preparation of 1,2-bis(4-Hydroxyphenyl)-2-hydroxypropane from 1,2-bis(4-Hydroxyphenyl)-2-chloropropane and Conversion to 4,4'-Dihydroxy-α-methylstilbene A. Production of Solution Containing 1,2-bis(4-Hydroxyphenyl)-2-chloropropane Phenol (1411.7 grams, 15.0 moles), chloroacetone (96.9%) (286.5 grams, 3.0 moles as chloroacetone), and methylene chloride (1789 grams) are added to a 5 liter glass reactor equipped with a chilled water condenser, mechanical stirrer, nitrogen purge (one liter per minute), thermometer, dropping funnel and jacket for circulating coolant over the reactor exterior. Stirring commences concurrent with cooling of the reactant solution to −10° C. Concentrated sulfuric acid (294.2 grams, 3.0 moles) is added to the dropping funnel, then dropwise addition to the stirred reactant solution commences over a 133 minute period so as to maintain the reaction temperature between −10° C. and −12° C. After 14.8 hours of post reaction at −12° C. to −13° C., high pressure liquid chromatographic (HPLC) analysis of a portion of the product using a UV detector set at 254 nm reveals the presence of the following area percent distribution of components in their relative order of elution: phenolsulfonic acids=0.26, phenol 68.4, 1,2,2-tris(4-hydroxyphenyl)propane=0.58, 4,4'-dihydroxy-α-methylstilbene=2.03, 1,2-(4-hydroxyphenyl)-2-chloropropane=25.3, with the balance as higher retention time compounds. At this time, chilled, deionized water (294.2 grams) is added to the stirred reaction product (3881.2 grams) inducing a maximum exotherm of −3° C., then after two minutes of mixing, the opaque, pale pink colored product is recovered and divided equally into a pair of 2 liter glass separatory funnels. The contents of each separatory funnel are allowed to settle and the aqueous and organic layers separated to recover 499.2 and 3361.3 grams, respectively. During this time, the maximum temperature reached in the organic layer was 3° C. and the HPLC analysis revealed essentially no change in the product: phenol=68.9, 1,2,2-tris(4-hydroxyphenyl)propane=0.66, 4,4'-dihydroxy-α-methylstilbene=1.95, 1,2-bis(4-hydroxyphenyl)-2-chloropropane=25.2, with the balance as higher retention time compounds.

B. In situ Preparation of 1,2-bis(4-Hydroxyphenyl)-2-hydroxypropane and Conversion to 4,4'-Dihydroxy-α-methylstilbene One half of the combined organic layer from A above is added to a 4 liter glass beaker equipped with magnetic stirring. The contents of each beaker are stirred, deionized water (250 milliliters) is added and heating commences. Sodium bicarbonate (45 grams) is added to the stirred mixture, and increases the pH from <1 to approximately 3 (pH paper used to test). A standardized pH probe was inserted into the mixture, and heating to reflux (50° C.) commenced. Once reflux was achieved, a pH of 5.94 was obtained and the solution turned yellow in color, indicative of the conversion of 1,2-bis(4-hydroxyphenyl)-2-chloropropane to 1,2-bis(4-hydroxyphenyl)-2-hydroxypropane. After two minutes at reflux, the pH decreased to 0.9 (1 by pH paper) and the pink color of the solution returned. A sample of the solution was obtained at this time and analyzed by HPLC revealing the conversion of 2.1 area percent 1,2-bis(4-hydroxyphenyl)-2-chloropropane and the concurrent formation of 1.7 area percent 1,2-bis(4-hydroxyphenyl)-2-hydroxypropane plus 1.5 area percent 4,4'-dihydroxy-α-methylstilbene. Continuation of the heating to 80° C. followed by workup completed the conversion of the 1,2-bis(4-hydroxyphenyl)-2-chloropropane and 1,2-bis(4-hydroxyphenyl)-2-hydroxypropane to 4,4'-dihydroxy-α-methylstilbene product. A slightly damp, crystalline 4,4'-dihydroxy-α-methylstilbene product (172.4 grams), free of 1,2-bis(4-hydroxyphenyl)-2-chloropropane and 1,2-bis(4-hydroxyphenyl)-2-hydroxypropane was recovered.

EXAMPLE 2

Isolation of Dry 1,2-bis(4-Hydroxyphenyl)-2-hydroxypropane Product

A wet cake containing 1,2-bis(4-hydroxyphenyl)-2-hydroxypropane is recovered from the reaction of a solution containing 1,2-bis(4-hydroxyphenyl)-2-chloropropane and calcium carbonate in aqueous media. HPLC analysis revealed the presence of 97.7 area percent 1,2-bis(4-hydroxyphenyl)-2-hydroxypropane, 1.8 area percent 4,4'-dihydroxy-α-methylstilbene and 0.5 area percent of an unknown compound. A portion of the wet cake is placed in an aluminum dish, then dried 20 hours at 25° C.–27° C. in a vacuum oven until a constant weight was achieved. The HPLC analysis of the recovered product is essentially unchanged: 97.7 area percent 1,2-bis(4-hydroxyphenyl)-2-hydroxypropane, 1.9 area percent 4,4'-dihydroxy-α-methylstilbene and 0.4 area percent of an unknown compound.

Comparative Example 1

Attempted Isolation of Dry 1,2-bis(4-Hydroxyphenyl)-2-hydroxypropane Product

A portion of the wet cake containing 1,2-bis(4-hydroxyphenyl)-2-hydroxypropane prepared in Example 2 above is dissolved in a minimum of isopropanol, then the resulting solution dried via the addition of anhydrous calcium carbonate, all at 21° C. The dry mixture is filtered to remove calcium carbonate and the resulting filtrate held under a stream of nitrogen to remove the isopropanol solvent. HPLC analysis of the resulting product demonstrates the presence of only 5.1 area percent 1,2-bis(4-hydroxyphenyl)- 2-hydroxypropane with the remainder of the sample containing 4,4'-dihydroxy-α-methylstilbene and coproducts.

Comparative Example 2

Attempted Synthesis of 1,2-bis(4-Hydroxyphenyl)-2-hydroxypropane from 1,2-bis(4-hydroxyphenyl)-2-chloropropane and Sodium Hydroxide/Sodium Bicarbonate A solution containing 1,2-bis(4-hydroxyphenyl)-2-chloropropane is produced using the method of Example 1A reported herein. In the reaction, phenol (188.2 grams, 2.0 moles), chloroacetone (96%) (38.6 grams, 0.4 mole as chloroacetone), and methylene chloride (238.5 grams) are added to a 1 liter glass reactor equipped with a chilled water condenser, mechanical stirrer, nitrogen purge (one liter per minute), thermometer, dropping funnel and jacket for circulating coolant over the reactor exterior. Concentrated sulfuric acid (39.2 grams, 0.4 moles) is added dropwise addition to the stirred reactant solution over an 18 minute period and so as to maintain the reaction temperature between –11 and –13° C. After 19 hours of post reaction at –12 to –13° C., HPLC analysis of a portion of the product reveals the presence of the following area percent distribution of components in their relative order of elution: phenolsulfonic acids=0.09, phenol=45.4, 1,2,2-tris(4-hydroxyphenyl)propane=1.25, 4,4'-dihydroxy-α-methylstilbene-undetected, 1,2-bis(4-hydroxyphenyl)-2-chloropropane=47.8, with the balance as higher retention time compounds. One half of the washed, –4° C. mixture containing 1,2-bis(4-hydroxyphenyl)-2-chloropropane (nominally 0.2 mole) is added over a two minute period to a 4 liter glass beaker containing a magnetically stirred 50° C. solution of the following: sodium hydroxide (8.0 grams, 0.20 mole); sodium bicarbonate (16.8 grams, 0.20 mole); deionized water (200 grams), isopropanol (300 grams). The stirred contents of the beaker are maintained with heating at 50 to 55° C., during which time, the methylene chloride present in the 1,2-bis(4-hydroxyphenyl)-2-chloropropane reactant is allowed to evaporate. After 4.3 hours, a sample of the mixture is obtained and analyzed by HPLC revealing complete conversion of 1,2-bis(4-hydroxyphenyl)-2-chloropropane (47.8 area percent) to product, as follows: 1,2-bis(4-hydroxyphenyl)-2-hydroxypropane=20.6 area percent, 2,3-bis(4-hydroxyphenyl)propene=15.5 area percent, 4,4'-dihydroxy-α-methylstilbene=4.1 area percent, with phenol and several other minor unknown coproducts comprising the balance.

EXAMPLE 3

Synthesis of 1,2-bis(4-Hydroxyphenyl)-2-hydroxypropane from 1,2-bis(4-Hydroxyphenyl)-2-chloropropane and Calcium Carbonate Methanesulfonic acid (192.24 grams, 2.0 moles) and phenol (107.58 grams, 1.143 moles) were weighed and rinsed into a jacketed flask using methylene chloride (50 grams). The flask was fitted with a nitrogen inlet and outlet, an addition funnel, thermometer and an overhead stirrer. Stirring was started and the speed was adjusted to approximately 200 rpm (±10 rpm). The mixture was cooled below –15° C., then chloroacetone (27.83 grams, 0.2857 mole) was added dropwise. The temperature was then adjusted to maintain the temperature at –10° C. to –120° C. and the mixture was stirred until gas chromatographic (GC) analysis showed the chloroacetone peak to be much less than the small dichloroacetone peak (present as a minor coproduct in the chloroacetone used). The mixture was chilled to –15° C. by cooling fully, then quenched by the addition of cold (–20° C.) methylene chloride (100 grams) followed by chilled deionized water (283 grams). The mixture was agitated until the temperature returned to 0° C., then the lower organic layer was drained off and poured into a second reactor containing a stirred mixture of isopropanol (294.46 grams), deionized water (196.31 grams) and calcium carbonate (34.32 grams) preheated to 50° C. The ,hydrolysis reaction was stirred under nitrogen and maintained at 50° C. for 4 hours. After completion, the mixture was diluted with an amount of deionized water and $NaHCO_3$ sufficient for azeotropic distillation, and concentrated by rotary evaporation to remove essentially all of the isopropanol and phenol, causing the precipitation of the 1,2-bis(4-hydroxyphenyl)-2-hydroxypropane product. The mixture was allowed to cool to room temperature and then filtered and rinsed with water to remove salt. The 1,2-bis(4-hydroxyphenyl)-2-hydroxypropane product was recovered as a damp cake in excess of 90% yield. HPLC analysis of a portion of the product revealed the presence of 97.7 area percent 1,2-bis(4-hydroxyphenyl)-2-hydroxypropane, 1.92 area percent 4,4'-dihydroxy-α-methylstilbene and 0.40 area percent of an unknown compound.

EXAMPLE 4

Synthesis of 1,2-bis(4-Hydroxyphenyl)-2-hydroxypropane from 1,2-bis(4-Hydroxyphenyl)-2-chloropropane and Magnesium Carbonate A solution containing 1,2-bis(4-hydroxyphenyl)-2-chloropropane is produced using the method of Example 1A reported herein. In the reaction, phenol (188.2 grams, 2.0 moles), chloroacetone (96%) (38.6 grams, 0.4 mole as chloroacetone), and methylene chloride (238.5 grams) are added to a 1 liter glass reactor equipped with a chilled water condenser, mechanical stirrer, nitrogen purge (one liter per minute), thermometer, dropping funnel and jacket for circulating coolant over the reactor exterior. Concentrated sulfuric acid (39.2 grams, 0.4 moles) is added by dropwise addition to the stirred reactant solution over a 42 minute period and so as to maintain the reaction temperature between −11° C. and −13° C. After 17 hours of post reaction at −12° C. to −13° C., HPLC analysis of a portion of the product reveals the presence of the following area percent distribution of components in their relative order of elution: phenolsulfonic acids=0.04, phenol=45.2, 1,2,2-tris(4-hydroxyphenyl)propane=1.25, 1,2-bis(4-hydroxyphenyl)-2-chloropropane=48.2, with the balance as higher retention time compounds. The washed, −4° C. mixture containing 1,2-bis(4-hydroxyphenyl)-2-chloropropane (nominally 0.4 mole) is added over a two minute period to a 4 liter glass beaker containing a magnetically stirred 50° C slurry of the following: magnesium carbonate (40.5 grams, 0.48 mole); deionized water (275 grams), isopropanol (410 grams). The stirred contents of the beaker are heated and maintained at a temperature of 50° C. to 55° C., during which time, the methylene chloride present in the 1,2-bis(4-hydroxyphenyl)-2-chloropropane reactant is allowed to evaporate. After 4.4 hours, a sample of the mixture is obtained and analyzed by HPLC revealing complete conversion of 1,2-bis(4-hydroxyphenyl)-2-chloropropane (48.1 area percent) to product, as follows: 1,2-bis(4-hydroxyphenyl)-2-hydroxypropane=44.0 area percent, 4,4'-dihydroxy-α-methylstilbene=0.38 area percent, with phenol and several other minor unknown coproducts comprising the balance.

EXAMPLE 5

Synthesis of 2,3-bis(4-Hydroxyphenyl)-2-hydroxybutane from 2,3-bis(4-Hydroxyphenyl)-2-chlorobutane Using Calcium Carbonate, Isopropanol and Water A solution containing 2,3-bis(4-hydroxyphenyl)-2-chlorobutane is produced using the method of Example 1A reported herein, except 3-chloro-2-butanone was substituted for chloroacetone. In the reaction, phenol (188.2 grams, 2.0 moles), 3-chloro-2-butanone (42.62 grams, 0.4 mole), and methylene chloride (238.5 grams) are added to a 1 liter glass reactor equipped with a chilled water condenser, mechanical stirrer, nitrogen purge (one liter per minute), thermometer, dropping funnel and jacket for circulating coolant over the reactor exterior. Concentrated sulfuric acid (39.2 grams, 0.4 moles) is added dropwise to the stirred reactant solution over a five minute period and so as to maintain the reaction temperature between −8° C. and −9° C. After 15.5 hours of post reaction at −9° C. to −13° C., HPLC analysis of a portion of the product reveals the presence of the following area percent distribution of components in their relative order of elution: phenolsulfonic acids=0.12, phenol=69.4, unknown=10.7, 2,3-bis(4-hydroxyphenyl)-2-chlorobutane= 19.5. One half of the washed, −4° C. mixture containing 2,3-bis(4-hydroxyphenyl)-2-chlorobutane (nominally 0.2 mole) is added over a two minute period to a 1 liter glass beaker containing a magnetically stirred 70° C. slurry of the following: calcium carbonate (24.0 grams, 0.24 mole); deionized water (137.5 grams), isopropanol (205 grams). The stirred slurry in the beaker is maintained with heating at 70° C., during which time, the methylene chloride present in the 2,3-bis(4-hydroxyphenyl)-2-chlorobutane reactant is allowed to evaporate. After 77 minutes, a sample of the mixture is obtained and analyzed by HPLC revealing complete conversion of 2,3-bis(4-hydroxyphenyl)-2-chlorobutane to 2,3-bis(4-hydroxyphenyl)-2-hydroxybutane (phenol and the unknown component still present and unchanged).

EXAMPLE 6

Synthesis of 2,3-bis(4-Hydroxyphenyl)-2-hydroxybutane from 2,3-bis(4-Hydroxyphenyl)-2-chlorobutane Using Calcium Carbonate and Water The remaining one half of the washed, −4° C. mixture containing 2,3-bis(4-hydroxyphenyl)-2-chlorobutane (nominally 0.2 mole) from Example 5 above is added over a two minute period to a 1 liter glass beaker containing a magnetically stirred 70° C. slurry of the following: calcium carbonate (24.0 grams, 0.24 mole) and deionized water (137.5 grams). The stirred slurry in the beaker is maintained with heating at 70° C., during which time, the methylene chloride present in the 2,3-bis(4-hydroxyphenyl)-2-chlorobutane reactant is allowed to evaporate. After 97 minutes, a sample of the mixture is obtained and analyzed by HPLC revealing complete conversion of 2,3-bis(4-hydroxyphenyl)-2-chlorobutane to 2,3-bis(4-hydroxyphenyl)-2-hydroxybutane (phenol and the unknown component still present and unchanged).

EXAMPLE 7

Conversion of 1,2-bis(4-Hydroxyphenyl)-2-hydroxypropane to 4,4'-Dihydroxy-α-methylstilbene A portion (0.121 gram) of the wet cake containing 1,2-bis(4-hydroxyphenyl)-2-hydroxypropane prepared in Example 3 was dissolved in an isopropanol and deionized water solution (1 milliliter) and sealed into a glass vial. The isopropanol and deionized water solution was prepared by combining isopropanol (100 grams) and deionized water (25 grams). The sealed vial is placed into an oven which has been preheated to 50° C. After 15.5 hours at 50° C., a sample of the mixture is obtained and analyzed by HPLC using calibrated response factors to reveal the following: 1,2-bis (4-hydroxyphenyl)-2-hydroxypropane=0.8 weight % cis- and trans-4,4'-dihydroxy-α-methylstilbene=80.7 weight % 2,3-bis(4-hydroxyphenyl)propene=13.5 weight % cis- and trans-1,2,4,5-tetrakis(4-hydroxyphenyl)-4-methylpentene= 5.0 weight %.

After 63 hours at 50° C., a sample of the mixture is obtained and analyzed by HPLC using calibrated response factors to reveal the following: 1,2-bis(4-hydroxyphenyl)-2-hydroxypropane=0.4 weight % cis- and trans-4,4'-dihydroxy-α-methylstilbene=92.5 weight % 2,3-bis(4-hydroxyphenyl)-propene=1.7 weight % cis- and trans-1,2, 4,5-tetrakis(4-hydroxyphenyl)-4-methylpentene=5.4 weight %

EXAMPLE 8

Conversion of 1,2-bis(4-Hydroxyphenyl)-2-hydroxypropane to 4,4'-Dihydroxy-α-methylstilbene Using Sodium Hydrogen Sulfate Catalyst A portion (0.121 gram) of the wet cake containing 1,2-bis(4-hydroxyphenyl)-2-hydroxypropane prepared in Example 3, sodium hydrogen sulfate (0.0051 gram) was dissolved in an isopropanol and deionized water solution (1 milliliter) and sealed into a glass vial. The isopropanol and deionized water solution was prepared by combining isopropanol (100 grams) and deionized water (25 grams). The sealed vial is placed into an oven which has been preheated to 50° C. After 63 hours at 50° C., a sample of the mixture is obtained and analyzed by HPLC using calibrated response factors to reveal the following: 1,2-bis(4-hydroxyphenyl)-2-hydroxypropane=3.4 weight % cis- and trans-4,4'- dihydroxy-α-methylstilbene=82.0 weight % 2,3-bis(4-hydroxyphenyl)propene=13.3 weight % cis- and trans-1,2,4,5-tetrakis(4-hydroxyphenyl)-4-methylpentene=1.3 weight %.

What is claimed is:

1. A process for producing a compound having the structural Formula I

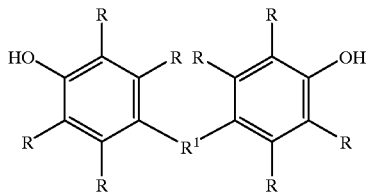

wherein R is independently selected from the group consisting of hydrogen, a hydrocarbyl group having from 1 to about 12 carbon atoms, a hydrocarbyloxy group having from 1 to about 12 carbon atoms, a halogen atom, and a nitro group, $R^1$ is a hydroxyl substituted aliphatic group having from 3 to about 8 carbon atoms; said process comprising reacting a compound having the structural Formula II

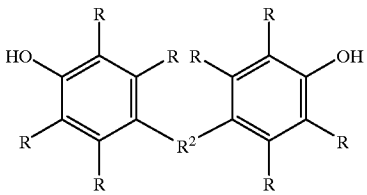

wherein R is as described above and $R^2$ is a halogen substituted aliphatic group having from 3 to about 8 carbon atoms, with a base and water, wherein
   (1) the base is selected from the group consisting of an alkali metal carbonate, alkaline earth metal carbonate, an alkali metal bicarbonate, an alkaline earth metal bicarbonate, and mixtures thereof;
   (2) the equivalent ratio of base to halogen in the halogen substituted aliphatic group is from about 0.9:1 to about 5:1; and
   (3) the amount of water is from about 20 to about 500 percent by weight of the combined weight of the compound of Formula II and water.

2. The process of claim 1 wherein each R is hydrogen.

3. The process of claim 1 wherein the halogen substituted aliphatic group is chlorine substituted aliphatic group.

4. The process of claim 1 wherein $R^2$ is —C(CH$_3$)(Cl)—CH$_2$—.

5. The process of claim 1 wherein the base is selected from the group consisting of lithium carbonate, sodium carbonate, potassium carbonate, calcium carbonate, strontium carbonate, cesium carbonate, rubidium carbonate, barium carbonate, magnesium carbonate, lithium bicarbonate, sodium bicarbonate, potassium bicarbonate, cesium hydrogen carbonate, rubidium acid carbonate, and hydrates and mixtures thereof.

6. The process of claim 5 wherein the base is selected from the group consisting of magnesium carbonate, calcium carbonate, strontium carbonate and mixtures thereof.

7. The process of claim 1 wherein the equivalent ratio of base to halogen in the halogen substituted aliphatic group is from about 1:1 to about 2:1.

8. The process of claim 1 wherein the equivalent ratio of base to halogen in the halogen substituted aliphatic group is from about 1.1:1 to about 1.5:1.

9. The process of claim 1 wherein the amount of water is from about 40 to about 300 percent by weight of the combined weight of the compound of Formula II and water.

10. The process of claim 1 wherein the amount of water is from about 60 to about 150 percent by weight of the combined weight of the compound of Formula II and water.

11. The process of claim 1 which further comprises employing a polar protic solvent.

12. The process of claim 11 wherein the polar protic solvent is selected from the group consisting of aliphatic alcohols, glycols, glycol ethers, and mixtures thereof.

13. The process of claim 12 wherein the polar protic solvent is selected from methanol, ethanol, n-propanol, isopropanol, n-butanol, isobutanol, t-butanol, t-amyl alcohol, ethylene glycol, ethylene glycol monomethylether, ethylene glycol monoethylether, propylene glycol monomethylether, and mixtures thereof.

14. The process of claim 13 wherein the polar protic solvent is selected from ethanol, n-propanol and isopropanol.

15. The process of claim 1 which further comprises recovering the compound of Formula I by azeotropic distillation.

16. The process of claim 1 which further comprises adding an amount of water sufficient to facilitate azeotropic distillation and then recovering the compound of Formula I by azeotropic distillation.

17. The process of claim 16 which further comprises drying the compound of Formula I at a temperature of below about 30° C. at a reduced pressure.

18. A process for producing a compound having the structural Formula III,

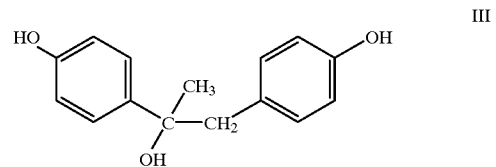

said process comprising reacting a compound having the structural Formula IV

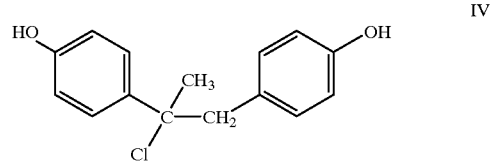

with a base, water, and a polar protic solvent, wherein
   (1) the base is selected from the group consisting of alkali metal carbonate, alkaline earth metal carbonate, alkali metal bicarbonate, alkaline earth metal bicarbonate, and mixtures thereof;
   (2) the equivalent ratio of base to halogen in the aliphatic group is from about 0.9:1 to about 5:1; and
   (3) the amount of water in the mixture of base, water, and polar protic solvent is from about 20 to about 500 percent by weight of the combined weight of the compound of Formula IV and water.

19. The process of claim 18 wherein
(1) the base is selected from the group consisting of magnesium carbonate, calcium carbonate, strontium carbonate, and mixtures thereof; and
(2) the polar protic solvent is selected from the group consisting of aliphatic alcohols, glycols, glycol ethers, and mixtures thereof.

20. The process of claim 19 which further comprises recovering the compound of Formula III by azeotropic distillation.

21. The process of claim 19 wherein the amount of solvent is from about 50 to about 300 weight percent of the combined weight of the compound of compound of Formula IV and solvent.

22. The process of claim 1 which further comprises converting the compound having the structural Formula I to the corresponding stilbene compound.

23. The process of claim 18 which further comprises converting the compound having the structural Formula III to the corresponding stilbene compound.

* * * * *